United States Patent
Hoffmann et al.

(10) Patent No.: US 10,463,806 B2
(45) Date of Patent: Nov. 5, 2019

(54) INJECTION DEVICES

(71) Applicant: REPLICEL LIFE SCIENCES, Vancouver (CA)

(72) Inventors: Rolf Hoffmann, Freiburg (DE); Martin Hohlrieder, Feldkirch (AT)

(73) Assignee: REPLICEL LIFE SCIENCES, Vancouver (CA)

( * ) Notice: Subject to any disclaimer, the term of this patent is extended or adjusted under 35 U.S.C. 154(b) by 0 days.

(21) Appl. No.: 15/481,620

(22) Filed: Apr. 7, 2017

(65) Prior Publication Data

US 2018/0021523 A1 Jan. 25, 2018

Related U.S. Application Data

(63) Continuation of application No. 14/375,205, filed as application No. PCT/CA2013/050074 on Jan. 31, 2013, now Pat. No. 9,616,182.

(30) Foreign Application Priority Data

Jan. 31, 2012 (EP) ..................................... 12153248

(51) Int. Cl.
*A61M 5/32* (2006.01)
*A61M 5/42* (2006.01)

(52) U.S. Cl.
CPC ............ *A61M 5/322* (2013.01); *A61M 5/427* (2013.01)

(58) Field of Classification Search
CPC ............................... A61M 5/427; A61M 5/46

USPC ................................................. 604/116, 117
See application file for complete search history.

(56) References Cited

U.S. PATENT DOCUMENTS

| | | | |
|---|---|---|---|
| 1,991,103 A | 2/1935 | King | |
| 6,391,005 B1 | 5/2002 | Lum | |
| 6,569,115 B1 | 5/2003 | Barker et al. | |
| 8,377,032 B2 | 2/2013 | Bates | |
| 2008/0294096 A1 | 11/2008 | Uber et al. | |
| 2009/0093761 A1 | 4/2009 | Sliwa | |
| 2010/0049126 A1 | 2/2010 | Bronfeld | |
| 2011/0054390 A1 | 3/2011 | Searle | |

FOREIGN PATENT DOCUMENTS

| | | |
|---|---|---|
| WO | WO 1991/000747 | 1/1991 |
| WO | WO 1993/002720 | 2/1993 |
| WO | WO 1994/023777 | 10/1994 |
| WO | WO 2002/083216 | 10/2002 |

OTHER PUBLICATIONS

Extended European Search Report issued in European Application No. 12153248.5, dated Jun. 21, 2012.
International Preliminary Report on Patentability issued in International Application No. PCT/CA2013/050074, dated Aug. 5, 2014.
International Search Report and Written Opinion issued in International Application No. PCT/CA2013/050074, dated May 17, 2013.

*Primary Examiner* — Deanna K Hall (57) ABSTRACT

The invention relates to an injection device. Exemplary embodiments of the invention comprise an application element, an injection needle, an injection needle housing, a drive system for the injection movement, and a retraction system. In exemplary embodiments, a substance is injected during the retraction movement of the injection needle.

8 Claims, 8 Drawing Sheets

INJECTION DEVICES

CROSS-REFERENCE TO RELATED APPLICATIONS

This application is a continuation of U.S. application Ser. No. 14/375,205, filed Jul. 29, 2014, as a national phase application under 35 U.S.C. § 371 of International Application No. PCT/CA2013/050074, filed Jan. 31, 2013, which claims priority to European Application No. 12153248.5, filed Jan. 31, 2012. The entire text of each of the above referenced disclosures is specifically incorporated herein by reference.

FIELD OF THE INVENTION

The present invention relates generally to injection devices, and more specifically, to devices which are suitable for injecting, delivering or administering a variety of substances, including cells, into tissue.

BACKGROUND OF THE INVENTION

It is sometimes desirable to inject a substance into a subject with more precision than a typical syringe. In view of the presence of different layers, for example in a human being, it may be necessary to deliver a substance very precisely within just one distinct tissue layer. Different layers are distinguishable such as skin, mucosa, subcutis, fascia, muscle, nerves, or joints. For example, human skin comprises several different layers. The epidermis is the outer skin layer with a thickness of about 30 to 2000 µm. The dermis is located beneath the epidermis with a thickness of about 500 to 1500 µm. The subcutis is located beneath the dermis with a thickness of about 500 to 30,000 µm. In certain applications, it is desirable to specifically deliver substances such as cells to specific locations within the skin.

It is necessary to provide means that allow that substances such as cells are injected in the desired physiological tissue. As one particular example, in the field of biological hair research there is a need for the accurate application of so called "dermal sheath cup" cells ("DSC") which have potential for hair follicle regenerating. Similar demands exist concerning further injection applications. For example the injection within the skin during cosmetic or aesthetic treatment requires further distinct means for the injection.

A further application concerns the injection into muscle tissue, joints, fascia, fat tissue, cartilage, submucosal tissues, or tendons. Such applications are often necessary after injuries which occur during sports or exercises. There is a constant need to treat tissue and distinct layers from the outside in a simple and reliable way.

The application of substances (e.g., liquids, biologics, or cell suspensions) within the dermis, epidermis or subcutis as well as muscle tissue layers or tendons requires a skilful handling by a medical doctor. In addition, the application of such substances can involve distinct requirements. For example, with respect to cells there is a need to deliver them as near to the respective tissue layer which resembles the physiological tissue layer of these cells in situ as possible. Secondly, there is also a need to apply the cells in a very careful way. In particular cells, such as stem cells or freshly prepared primary cells, are sensitive in view of pressure which arises during the application. Such pressure occurs for example when cells are applied via a narrow cannula which results in a high compression of the cells. Such a compression and the resulting shear stress which acts on the cells are harmful. The consequence of this can be that cells are severely damaged and probably even loose their viability.

It is possible to apply cells to the scalp of a subject with a standard syringe having a needle of a distinct size and length. This has however the disadvantage that it is not possible to apply the cells in a constant manner since the needle is shifted each time the injection site is changed. Accordingly, the angle between the injection needle and the scalp surface is not constant and will be very likely altered during each injection. Further, the injection depth will very likely vary during the different injections, since there is no measure of how deep the injection has to be performed if it is conducted with a standard syringe having an injection needle which is only guided by hand.

WO 02/083216 A1 describes a device and a method for the intradermal injection of substances. The afore-mentioned device allows the injections in a defined depth of penetration which allow an intradermal delivery, wherein the needle is injected perpendicular to the plane of the skin.

WO 94/23777 A1 describes an intradermal injection device which allows also a subcutaneous injection and foresees the application of a vacuum.

However, none of the devices of the prior art allows the delivery of liquid substances, such as cells, without the application of pressure or shear-stress. Furthermore, none of the devices of the prior art allows the application of liquid substances, such as cells, in a reliable way which ensures that the application occurs in the optimal physiologic site.

The application of cells to, for example, the scalp of a subject, requires distinct requirements as outlined above. Further, it is necessary that the cells are applied within a single layer or region and in a distributed manner. Accordingly, it is desired that the cells are not injected in punctual form but preferably in a more dispersed way.

Therefore, there is a need to provide a device which overcomes the problems as described above and which allows the delivery of substances, in particular biological substances, such as cells, in a careful manner and at the desired physiological site in a reliable and reproducible way. This underlying technical problem is solved with the injection device as defined within the claims.

The injection device according to the present invention provides distinct advantages over the prior art since liquid substances and cell suspensions can be applied in a careful and gentle way and the delivery is conducted in the desired physiologic tissue layer.

For the purpose of illustration of the present invention, the present invention is shown in illustrative form, it being understood however, that the invention is not limited to the precise form shown in the figures or examples.

SUMMARY OF THE INVENTION

Briefly stated, the present invention provides a devices for injecting (e.g., administering, infusing, introducing or delivering) a variety of substances to a subject. Representative substances include, for example, liquids, suspensions, drugs, biologics and cells. Within one aspect of the invention injection devices (100) are provided for introducing a substance into the body of a subject, the injection device comprising: an application element (10), at least one injection needle (32), an injection needle housing (20), a drive system (25) for the injection movement and a retraction system (35) for the retraction movement, wherein the substance is injected during the retraction movement of the injection needle. Within one embodiment the drive system (25) and the retraction system (35) comprises a micro linear pusher. Within another embodiment the drive system (25) comprises a first guide rail (60), a second guide rail (70) and a first slide (30). Within yet another embodiment the drive system (25) and retraction system (35) comprises a ratchet mechanism.

Within other embodiments of the invention the substance is a liquid which is conducted with an injection system comprising a motor (3), a lead screw and a screw nut. Within further embodiments the injection needle housing (20) comprises two, three, four, five or more injection needles. Within yet another embodiment all injection needles are injected simultaneously.

Other embodiments of the invention include injections devices wherein the application element (10) is a cooling plate, preferably a Peltier element. Within further embodiments, the injection depth of the injection needle (32) is in a range from preferably 0.5 mm to 5 cm, preferably 0.5 mm to 4 cm, preferably 0.5 mm to 3 cm, preferably 0.5 mm to 2 cm, preferably 0.5 mm to 1 cm, preferably 0.5 mm to 5.5 mm, preferably from 1.5 mm to 4.0 mm, more preferably from 2.0 mm to 3.5 mm, most preferably 3.4 mm. Within yet other embodiments the retraction movement of the injection needle (32) different injection volumes are injectable in different injection depths.

Within other embodiments of the invention the angle between the injection needle (32) and the application element (10) is adjustable and the angle is preferably in the range from preferably 10 degrees to 90 degrees, preferably 10 degrees to 80 degrees, preferably 10 degrees to 70 degrees, preferably 10 degrees to 60 degrees, preferably 10 degrees to 50 degrees, 10 degrees to 40 degrees, preferably from 15 degrees to 25 degrees, more preferably 20 degrees. Within a further embodiment the opening (36) of the injection needle (32) is adjusted in an upward direction. Within yet another embodiment the injection device comprises means for lighting.

Within other embodiments the application element (10) comprises means for fastening the device to the body of the subject. Within further embodiments the injection device further comprise an optical device such as a camera or a laser.

The details of one or more embodiments are set forth in the description below. Other features, objects and advantages will be apparent from the description, the drawings, and the claims. In addition, the disclosures of all patents and patent applications referenced herein are incorporated by reference in their entirety.

DETAILED DESCRIPTION OF THE INVENTION

A first subject-matter of the present invention relates to the provision of an injection device which allows the precise and targeted delivering of cells, as one example of a substance, in dermal tissue layers.

In a preferred embodiment of the present invention, the provision of an injection device for introducing a substance into the body of a subject is foreseen, wherein the injection device is comprising an application element, at least one injection needle, an injection needle housing, a drive system for the injection movement, and a retraction system, wherein liquid is injected during the retraction movement of the injection needle.

With the injection device of the present invention it is foreseen that the substance, for example cells within a liquid solution, are only applied during the retraction movement of the injection needle. The retraction movement is conducted in a slow and constant form, which provides the advantage that the substance, and in particular cells, are applied without any pressure or shear stress. It has to be noted that in particular the retraction mechanism and the careful delivery of the cells has the effect that the cells are in a viable and healthy state after the application. This has the advantage that the injection device of the present invention improves the conditions of cell delivery and thus improves the expectations of success in the treatment of the subject. This beneficial application of the cells is conducted with the provision of an injection device which comprises a drive mechanism as well as a retraction mechanism. The drive mechanism and also the retraction mechanism according to the present invention allow a moderate and constant application of the liquid or the cells. Furthermore, the application with the injection device provides a gentle delivery of the substance (e.g. cells) which inhibits an undesired reflux from the injection site as it occurs in so called "wet injections".

Furthermore, the injection device according to the present invention has the advantage that the injection can be conducted in a manner which avoids the injury of a blood vessel.

Due to the distinct construction of the injection needle within the injection device it is inhibited that a blood vessel can be punctured. Even in the unexpected case that a blood vessel would have been punctured, the injection needle is retracted during the retraction movement. Thus, a punctured blood vessel would be released during the retraction movement of the injection needle. Accordingly, an injection in a blood vessel is inhibited with the injection device of the present invention. Therefore, the injection device of the present invention provides a safe delivery of liquid substances. Nevertheless, in the case a direct injection in a blood vessel is actually intended, the injection device according to the present invention can also be used in such an application form.

With the injection device of the present invention it is foreseen that not only a distinct site is treated with the injection. Moreover, it is also foreseen that a defined distribution region is treated with the injection device of the present invention. This is achieved with the movement of the injection needle during the retraction movement. The retraction movement is conducted over a defined distance from the end point of the injection back to the surface of the injection site. Therefore, the substance is not deposited at a single injection point. Rather, the deposition occurs in the complete region of needle retraction and not only at a singular injection point. This complete injection region is defined by the length of the injection path during the retraction movement. Both the injection path and its depth are defined by the device.

In a further preferred embodiment of the invention, the drive system and the retraction system of the injection device is a "micro linear pusher". The micro linear pusher may be activated manually or by means of an electronic system.

In the context of the present invention, the term "micro linear pusher" has to be understood as an element which functions as a movement axis for the positioning and guidance of a slide as a tool holder in a straight line. The micro linear pusher according to the present invention exerts the forward and reverse movement of the injection needle. Accordingly, it is foreseen that the micro linear pusher drives the injection needle in forward and reverse direction. Therefore, in a preferred embodiment of the present invention the micro linear pusher functions as a drive system and as a retractions system.

According to a preferred embodiment of the present invention it is foreseen that the micro linear pusher is activated electronically in addition to being activated manually.

In a preferred embodiment of the present invention the injection device is an injection which is completely manually operated and not powered by electricity.

Accordingly, in a further preferred embodiment of the present invention it is foreseen that the drive system of the present invention comprises a first guide rail, a second guide rail and a first slide. In this distinct preferred embodiment of the present invention it is foreseen that this drive system functions only mechanically without electronic activation.

Further preferred, the injection device is driven by hydraulic means, such as a hydraulic pump. In a further particularly preferred embodiment the hydraulic means are not included in the injection needle housing but are provided outside of the injection device. Accordingly, in the case the hydraulic means are a hydraulic pump it is foreseen that this is deposited on the floor and can be operated by foot. This provides the advantage that the injection device is reduced in size and weight.

In a preferred embodiment of the manually operated injection device of the present invention the drive system and the retraction system comprises a ratchet mechanism. Preferably, such a ratchet mechanism is composed of distinct components. Accordingly, it is foreseen that the ratchet mechanism is composed of a first guide rail, a second guide rail, wherein the first and the second guide rail having grooves on their surface and are positioned parallel to each other. Further, the ratchet mechanism comprises a first slide and a second slide, wherein the first and second slide are guided on the first and second guide rail. The ratchet mechanism further is composed of a first and a second leaf spring, whereby the leaf springs engage with the grooves of the guide rails and provide a retraction movement. In accordance with the present invention it is foreseen that the injection of a substance occurs during this retraction movement of the injection needle.

In a further preferred embodiment of the invention it is foreseen that injection of a substance is conducted with an injection system comprising a motor, a lead screw and a screw nut. According to this preferred embodiment of the present invention it is foreseen that the injection is conducted via the forward movement of the piston of a syringe which is included in the injection device.

In a further preferred embodiment of the present invention the drive system and/or the retraction system comprises a motor with a lead screw and a screw nut. Accordingly, it is foreseen that preferably the forward movement of the injection needle as well as the injection of the substance during the retraction movement are performed with two separate motors.

In a further preferred embodiment of the present invention the injection of the substance is performed with a micro linear pusher. According to this preferred embodiment it is foreseen that the drive system and the injection of the liquid during the retraction movement of the injection needle is performed with two separate micro linear pushers.

Accordingly, in a preferred embodiment of the present invention it is foreseen that a combination of two micro linear pushers or a combination of two motors with lead screws and screw nuts as drive system and retraction system as well as injection system is foreseen. Further preferred is the combination of one micro linear pusher in combination with one motor with lead screw and screw nut as actuation for the drive system and retraction system as well as for the injection system during the retraction movement.

Preferably, it is foreseen that in the case the injection system comprises a motor that the motor leads to the rotation of the lead screw. The screw nut remains rotation-locked and transforms the rotation movement into a linear movement. The screw nut thereby exerts a push which results in the injection of the liquid through the injection needle.

According to the present invention in the case the drive system and/or the retraction system include a micro linear pusher and/or a motor which are driven electronically, it is foreseen that the micro linear pusher and the motor are configured by a software-assisted programming in such a way that the injection of the liquid is only conducted during the retraction movement of the injection needle.

In a further preferred embodiment the injection device of the present invention comprises two, three, four, five or more injection needles.

Preferably, it is foreseen that all injection needles are injected simultaneously.

In a further preferred embodiment of the present invention, it is foreseen that not all of the injection needles are injected simultaneously.

Further preferred, the different injection needles can be injected independently in a distinct depth with a distinct angle.

In a further preferred embodiment of the present invention, the application element of the present invention is a cooling plate. In a preferred embodiment the cooling plate is a Peltier element.

The Peltier element allows the provision of a thermoelectric cooler (TEC). Accordingly, such a thermoelectric cooler functions as a cooling plate. This provides the advantage that the tissue of the subject is cooled, in particular at the site where the injection is conducted. The Peltier element allows advantageously that the cooling applies not only at the surface where the injection is conducted but also in the underlying tissue. A reduced pain sensitivity of the patient during the injection is thereby achieved. In a further preferred embodiment of the present invention, a cooling is achieved with a water-cooling. In a further preferred embodiment of the present invention it is foreseen that the cooling is conducted with a container which is attached on the injection device of the present invention, wherein this container includes liquid nitrogen or alcohol. Further preferred it is foreseen that a superficial anaesthetic, such as a freezing spray, is included in the container and applied to the surface before the injection with the injection device of the present invention is conducted.

In a further preferred embodiment of the invention the application element has round or horseshoe-shaped form. Further shapes may be applicable for a skilled person. Preferably, it is foreseen that the application element is constructed to provide an opening for the injection needle. In a further preferred embodiment of the present invention, the application element includes several openings which allow the passing through of several injection needles during the injection.

Further preferred, the application element may be surrounding the injection needle during the injection. Preferably, the application element is preferably a Peltier element which provides cooling in deeper injection regions, such as muscle tissue or tissue which is adjacent to tendons.

In a further preferred embodiment of the present invention it is foreseen that the application element is a head section with an opening.

Preferably, the application element of an injection device which is manually operated has a head section which has an upper part and a lower part, wherein the upper part of the head section comprises a magnifying glass. The use of a magnifying glass has the advantage that the site of injection can be visualized in a conveniently manner. Such an improved visualization then allows a repetitive injection in the same site.

In a further preferred embodiment, the upper part of the head section contains only a free opening.

In a further preferred embodiment, it is foreseen that the head section is concave shaped. The provision of a concave shape provides the possibility to configure the head section of the injection device to the skin surface of the subject, for example the scalp of a subject.

In a preferred embodiment, the injection device of the present invention achieves an injection in the desired tissue layer to an injection depth in the range from 0.5 mm to 5 cm, 0.5 mm to 4 cm, 0.5 mm to 3 cm, 0.5 mm to 2 cm, 0.5 mm to 1 cm, 0.5 mm to 5.5 mm, preferably in a depth from 1.5 mm to 4.0 mm, more preferably in depth from 2.0 mm to 3.5 mm, most preferably in a depth of 3.4 mm. The injection depth is dependent on the distinct application. For example, the injection depth is preferably 3.4 mm in the case of DSC cell injection. In the case where fibroblasts or adipocytes are injected, the injection depth is preferably about 5.0 mm. Preferably, adipocytes may be used as a so called "filler" and injected in a depth which corresponds to a subcutaneous injection. Further, adipocytes may be injected in depth of about 3 to 4 mm. Preferably, injections into muscle tissue or in tendons may be conducted in a depth of about 2 cm to 3 cm up to 5 cm. The injection depth is defined by the length of the injection needle and is further defined by the angle of the injection.

It is included within the experience of a person skilled in the art to apply the respective injection depth dependent on the distinct type of substance and dependent on the desired application form and effect which should be achieved.

Preferably, the injection volume is applied in a constant manner during the retraction movement.

In a further preferred embodiment of the present invention, it is foreseen that different injection volumes are injectable with different injection depths during the retraction movement of the injection needle. Accordingly, preferably a first distinct volume is injected in a first site of, for example, 5.5 mm depth, then during the retraction movement of the injection needle a second volume is injected in a depth of, for example, 3.4 mm. Accordingly, in a preferred embodiment it is foreseen that the volume in the region which is treated during the injection is subdivided in different injection depths and during the retraction movement distinct volumes are injected in each of the injection depths.

In a preferred embodiment of the present invention it is foreseen that the injection device allows the application of different injection forms. Preferred injection forms are a bolus injection, an injection in a tadpole-like form, a continuously distributed injection over the length of the injection path with the application of the same volume during the retraction movement, or a combination of different injection forms.

The injection volumes can be varied at each distinct injection site of the distinct injection depth.

The range of the injection length defines the length of the injection path during the retraction movement of the injection needle. Accordingly, it is foreseen that the total injection length is defined by the length of the injection needle. Preferably, it is foreseen that the total injection length of the injection needle is in a range from 2.0 mm to 20 mm, preferably from 5.0 mm to 15 mm, more preferably 10 mm.

In a preferred embodiment of the present invention, the angle between the injection needle and the application element is adjustable.

Preferably, the angle between the injection needle and the application element is in the range from 10 degrees, to 90 degrees, 10 degrees to 80 degrees, 10 degrees to 70 degrees, 10 degrees to 60 degrees, 10 degrees to 50 degrees, 10 degrees to 40 degrees, preferably from 15 degrees to 25 degrees, more preferably 20 degrees.

In a preferred embodiment of the present invention, it is foreseen that the angle between the injection needle and the application element and/or the injection depth allow dermal application of the liquid.

Accordingly, the injection device of the present invention allows conducting the application of a substance, like a liquid, such as cells in a liquid medium, in a preferably constant manner with a fixed angle and a defined depth for each injection site. The application of a substance and in particular of cells, like DSC cells, in the scalp of a subject, has to be conducted in the dermal layer as particular tissue layers. Further application forms, such as injections in muscle tissue or in tendons require the injection within deeper layers. This is achieved with the injection device of the present invention which allows the injection with a defined angle and a defined depth which remains constant during each single injection.

In a particularly preferred embodiment of the present invention, the injection device provides an angle of 20 degrees in combination with an injection depth of less than 1 mm for the application of fat cells into a subject.

In a further particularly preferred embodiment of the present invention, the injection device provides an angle of constant 90 degrees in combination with an injection depth of at least 1 cm for the application of a substance into tendon cells. Preferably, the determination of the necessary injection depth is monitored by ultrasound.

It is foreseen with the injection device of the present invention that distinct injection angles are combined with distinct injection depths. Accordingly, it is foreseen that desired combinations of distinct injection angles with distinct injection depths can be adjusted with the injection device of the present invention. Preferred combinations of injection angles with injection depths are 20 to 30 degrees with 1 mm to 1 cm, 30 to 40 degrees with 1 mm to 1 cm, 40 to 50 degrees with 1 mm to 1 cm, 50 to 60 degrees with 1 mm to 1 cm, 60 to 70 degrees with 1 mm to 1 cm, 80 to 90 degrees with 1 mm to 1 cm.

In a preferred embodiment of the present invention, the diameter of the injection needle is in the range of 18 to 32 G, of 20 to 30 G, more preferably 24, 25 or 26 G. 26 G has a diameter of about 0.46 mm.

In a further preferred embodiment a syringe with a volume of 1 ml is used within the injection device of the present invention. Preferably, such a 1 ml syringe allows 6 injections of 166 µl. Syringes with 2, 5 or 10 ml may also be preferred. Further syringes with a bigger or smaller volume may also be used in a preferred embodiment of the present invention dependent on the particular use of the injection device.

Preferably, it is foreseen that the opening of the injection needle is adjusted in an upward direction. According to the present invention an upward direction means that the orientation of the injection needle is directed towards the surface or region where the injection occurs.

This provides the advantage that the cells can be applied in an optimal orientation within the distinct tissue layer. In the case the injected cells are for example DSC cells, the injection in an upward direction in the dermal layer is advantageous since the cells can more easily grow in the direction of the scalp. Thus, the outgrowth of hair is promoted with the injection of DSC cells into the scalp of a subject with the injection device of the present invention.

Preferably, the injection device is further comprised of means for lighting. Such lighting may be, but is not restricted to, LED (light-emitting diode) or other lighting appliances. The provision of lighting appliances allows a better visualisation and an easier determination of the distinct injection site. In a further preferred embodiment of the present invention, the means for lighting are included in the injection needle housing, such that the injection site is illuminated.

In a further preferred embodiment of the present invention, it is foreseen that further appliances, such as optic devices or a laser device is included in the injection needle housing. Preferably, the optic device is a camera, such as a video camera or a photographing apparatus.

In a preferred embodiment the injection device comprises an application element with fastening means for fastening the injection device to the subject. In a preferred embodiment of the present invention the fastening means comprise the application of a vacuum.

In a further preferred embodiment of the present invention, the fastening means include glue or a fixation frame.

In a further preferred embodiment, it is foreseen that the injection device of the present invention comprises a laser device. The laser device allows the projection of marked site for the injection on distinct sites of the surface, where the injection should be conducted. Further preferred it is foreseen that the laser device provides the projection of several marked sites, where the injection should be conducted. The marked sites from the laser device provide the advantage that the distance between the different injection sites can be constantly maintained. In a further preferred embodiment of the present invention, the use of one, two, three or more sources of a laser is foreseen. The provision of a laser has further the advantage that this laser can have an alternative penetrative function in comparison to the injection needle. Further, the laser provides the advantage that bleeding during the injection is inhibited or at least reduced. Furthermore, in a preferred embodiment of the present invention, it is foreseen that the laser is used in combination with the injection needle. Thus, it is preferably foreseen that the injection region is prepared with the laser. Due to this preparation, an injection channel can be formed wherein then the injection with the injection needle can be performed.

In a further preferred embodiment, the application element, the holder for the injection needle and the injection needle, are exchangeable. Accordingly, it is possible that for each subject the items that can only be used individually can be changed separately to fulfil hygienic standards.

The distinct construction of the injection device of the present invention inhibits that the user of the device may be unintentionally hurt by the injection needle since the needle is retracted within the injection needle housing during its starting position. Thus, the injection needle is not exposed all the time.

The present invention relates in particular to the use of the injection device of the present invention for the application of a substance, such as a liquid, into the tissue of a subject.

In a preferred embodiment of the present invention the substance is selected from the group consisting of cell suspension, gel-like materials, therapeutic substances, cosmetic substances, and diagnostic substances.

Cosmetic substances can include, but are not restricted to application of adipocytes as filler, the application of hyaluronic acid, or application of botulinus toxin (Botox, Btx) in the wrinkle treatment.

Therapeutic substances can include, but are not restricted to, antibiotics, anesthetics, analgesics, vaccines, antibodies.

In a preferred embodiment of the present invention it is foreseen that the cell suspension is mixed with growth factors. In a further preferred embodiment of the invention it is foreseen that the cell suspension is included in a gel-like structure. Preferably, such gel-like structures represent mixtures of extracellular matrix proteins which mimic the extracellular environment of distinct tissues. Further preferred is a gel-like structure such as hyaluronic acid.

Accordingly, preferably the injection device of the present invention is used to apply cells in a suspension or in a liquid medium to a subject.

In a preferred embodiment of the present invention, it is foreseen that the injection device is used for the application of a substance into a distinct tissue of a subject. In particular, it is preferably foreseen that the injection device is used for the application of cells into the skin, preferably as cell suspension, in the treatment of hair loss, alopecia, such as alopecia areata, or other symptoms associated with a lack of or too less hair. Further, the injection device of the present invention is preferably used for the application of a liquid such as a medicament, a cytokine or a growth factor into a subject. Preferably, this application of the liquid into a subject is conducted in connection with the treatment of hair loss, alopecia, such as alopecia areata, or other symptoms associated with a lack of or too less hair. In a further preferred embodiment of the present invention, the injection device is used for the application of a substance into a muscle of a subject. Further preferred, the injection device is used for the application of a substance into a tendon of a subject.

Generally, unless otherwise indicated, the materials for making the invention and/or its components may be selected from appropriate materials such as metal, metallic alloys, ceramics, plastics, etc.

In a distinct preferred embodiment of the present invention the provision of an injection device for introducing a substance into the body of a subject is foreseen, wherein the injection device is comprising an application element in form of a head section for the application of the injection device on the body of a subject, wherein the head section has an opening; an injection needle housing is coupled to the head section; a first slide comprising a holder for an injection needle which comprises a hollow injection needle which comes out during the injection from the injection needle housing through the opening from the head section, a holder for a syringe, which fits into the injection needle housing; a second slide comprising means for holding the piston of a syringe, and a release element, including means for releasing the second slide; a first guide rail having grooves on the surface which is fastened to the injection needle housing, and a second guide rail having grooves on the surface which is fastened to the first slide; wherein the first slide and the second slide are guided on the first guide rail and the second guide rail; the first slide is connectable to the second slide over a piston of a syringe; the second slide includes a first leaf spring which engages with the grooves of the first guide rail, thereby providing together with the first slide a drive mechanism for the injection movement, and the second slide comprises further a second leaf spring which engages with the grooves of the second guide rail, thereby providing together with the first slide and a spring included in the first slide a retraction mechanism for retracting the injection needle until the injection needle returns to its starting position.

According to this distinct preferred embodiment of the present invention it is foreseen that the first leaf spring engages with the grooves of the first guide rail and the second leaf spring engages with the grooves of the second guide rail. Due to the structure of the grooves in combination with the first and second leaf spring a ratchet mechanism is provided. The grooves on the surface of the first and second guide rails function as ratchets in combination with the first and second leaf springs. This allows the movement which is conducted by the drive mechanism and the retraction mechanism.

In particular it is foreseen that the drive mechanism allows the injection movement. This injection movement is conducted according to a distinct embodiment of the present invention with the movement of the first slide together with the first guide rail in injection direction. Thereby the first leaf spring clicks into position of one of the grooves of the first guide rail. Meanwhile the injection movement the spring included in the first slide is compressed. The retraction mechanism exhibits the opposite movement of the injection movement, namely the retraction movement. During the retraction movement, the second leaf spring clicks into position of one of the grooves of the second guide rail. The retraction movement is further assisted by the spring included in the first slide. The spring which is compressed during the injection movement removes its tension. Thus, the compressed spring allows during the release of the compression that the first slide is pushed away from the injection needle housing. Thereby the first slide is moved in the opposite direction from the injection direction and thus the injection needle is released and returns to its starting position. Further, during the retraction movement the piston of the syringe is compressed which allows the application of a liquid solution only during the retraction movement. The retraction movement assisted by the spring allows a slow and constant retraction movement which provides a careful delivery of the liquid solution during the application. During the retraction movement the distance between the first slide and the second slide is reduced since the retraction movement mediated over the ratchet mechanism of the second leaf spring and the grooves of the second guide rail exhibit the opposite direction in comparison to the injection movement of the ratchet mechanism of the first leaf spring and the grooves of the first guide rail.

In the context of the present invention a spring can be any component which exerts after deformation a respective restoring force.

Preferably according to a distinct embodiment of the present invention, it is foreseen that the drive mechanism provides a movement of the first slide over a distance which is defined by the holder of the syringe. Preferably, the movement is determined by a distinct form of the holder of the syringe. In a preferred embodiment of the present invention, the holder is constructed with a cut-out for a syringe leading into a protruding tube-formed element. This protruding tube-formed element fits into the injection needle housing. According to this preferred embodiment, the movement is defined by the size of the protruding tube-formed element. This provides an injection depth of the needle which is defined by the movement of the first slide.

Further preferred according to a distinct embodiment of the present invention it is foreseen that the injection device includes further a release element. According to a preferred embodiment of the invention the release element is part of the second slide. Preferably, the release element is constructed in a distinct geometrical form which allows that the second slide can be moved freely in the first and second guide rail. The releasing is conducted due to the structure of the release element which allows that the leaf springs detach from the first and second guide rail. This in turn allows that the second slide can be moved freely along the first and second guide rail.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

EXAMPLES

This description of embodiments of the present invention is exemplary in nature and is in no way intended to limit the invention or its application or uses.

Example 1: Mechanical Injection Device

Figure 1:
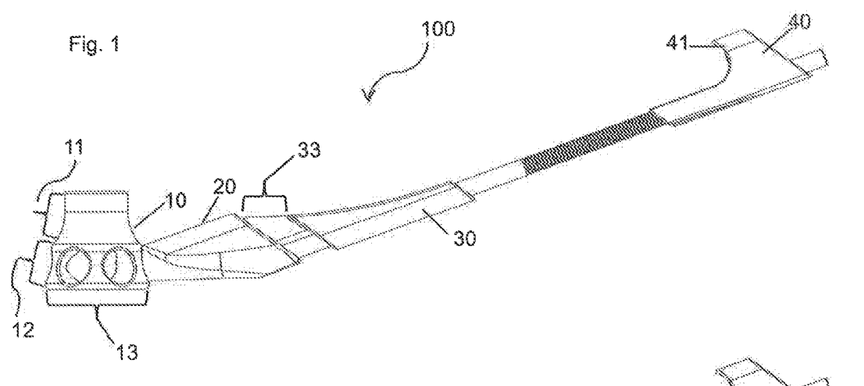
FIG. 1 shows a side view of a preferred embodiment of the injection device, wherein the injection needle is in its starting position.
Figure 2:
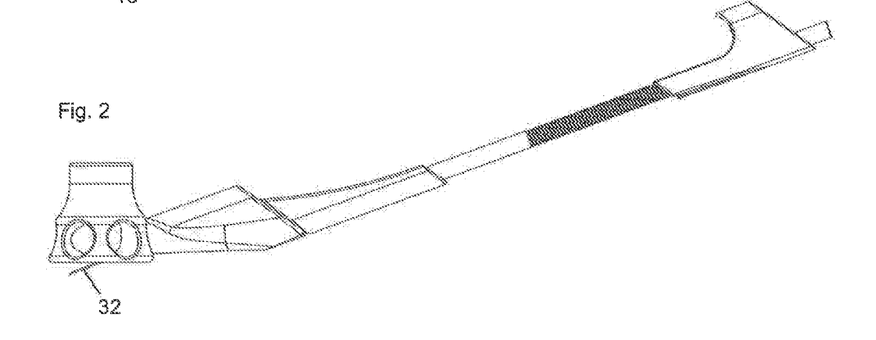
FIG. 2 shows a side view of a preferred embodiment of the injection device, wherein the injection needle is in its fully injected position.
Figure 3:
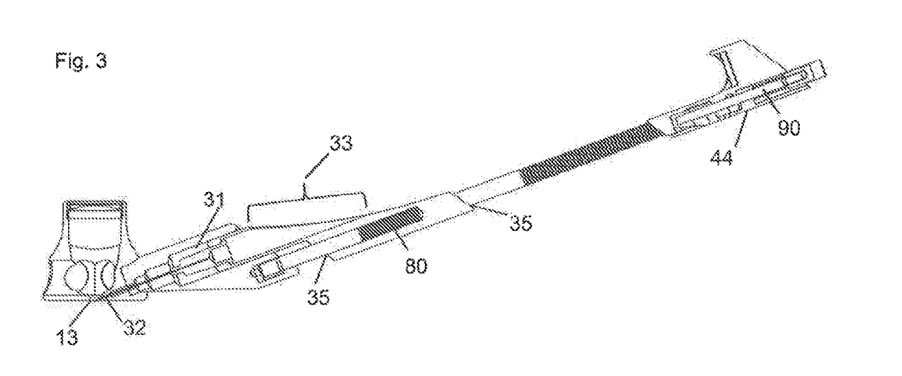
FIG. 3 shows a side view of a preferred embodiment of the injection device in longitudinal section with transparent view of the inside, wherein the injection needle is in its starting position.
Figure 4:
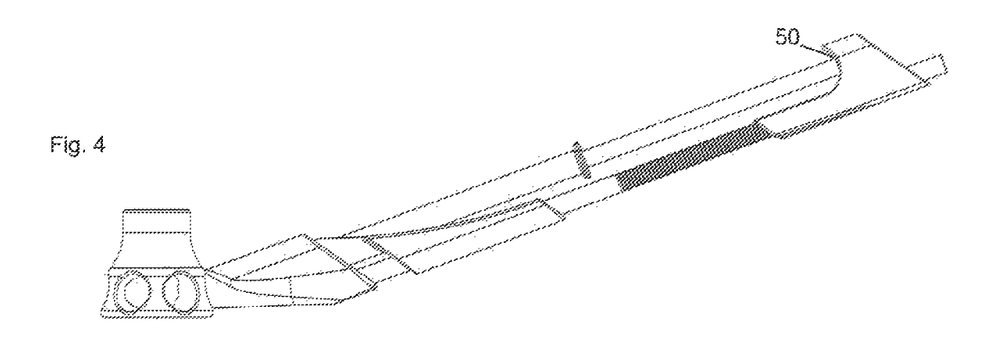
FIG. 4 shows a side view of a preferred embodiment of the injection device, wherein the injection device comprises a syringe with a piston which connects the first slide with the second slide. The distance between the first slide and the second slide is maximal due to the maximal extended piston.
Figure 5:
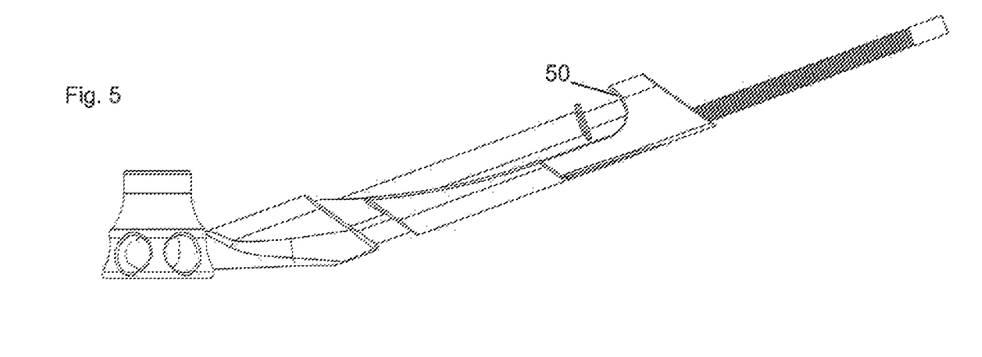
FIG. 5 shows a side view of a preferred embodiment of the injection device, wherein the injection device comprises a syringe with a piston which connects the first slide with the second slide. The distance between the first slide and the second slide is minimal due to the completely pressed in piston.
Figure 6:
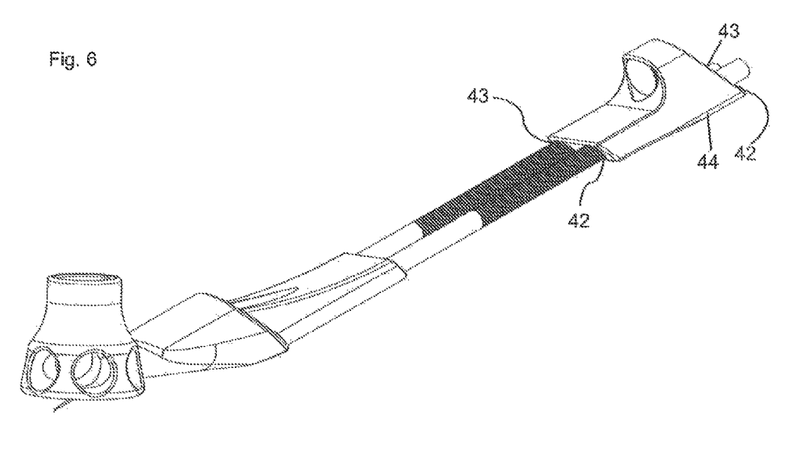
FIG. 6 shows a preferred embodiment of the injection device in perspective plan view of one side, wherein the injection needle is in its fully injected position.
Figure 7:
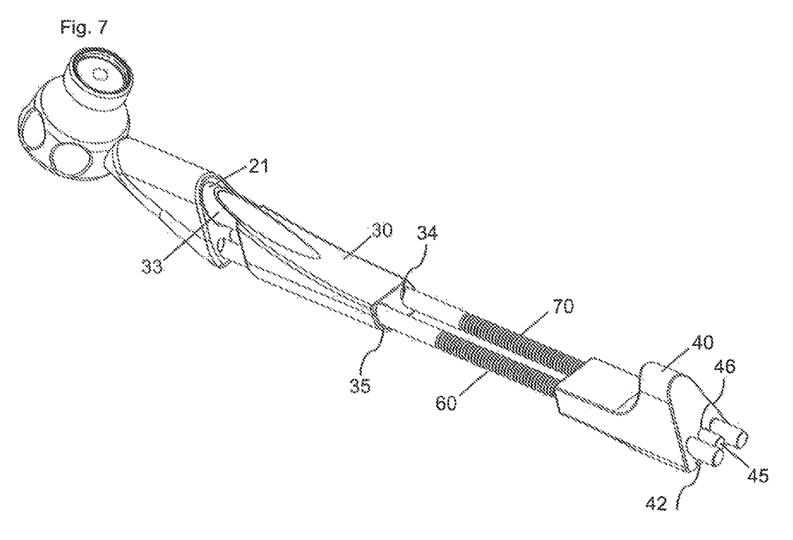
FIG. 7 shows a preferred embodiment of the injection device in perspective plan view of the top side of one side.
Figures 8A, 8C:
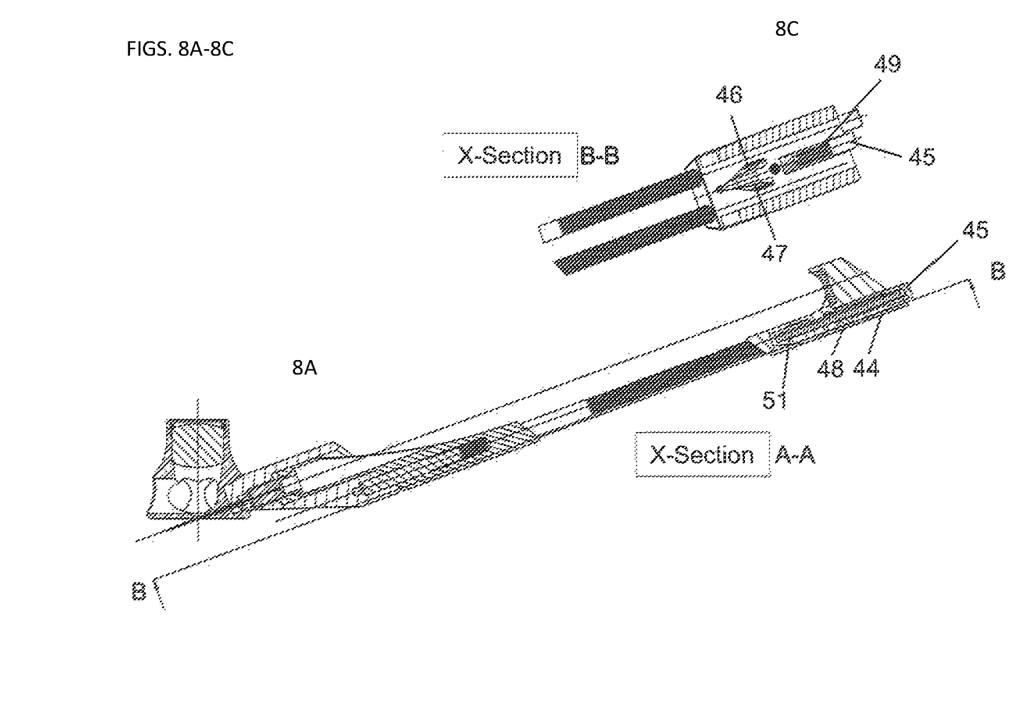
FIG. 8A shows a side view of a preferred embodiment of the injection device wherein the sectional planes A-A and B-B are indicated.
FIG. 8B and FIG. 8C show the cutting planes A-A and B-B in detail.
Figure 8B:
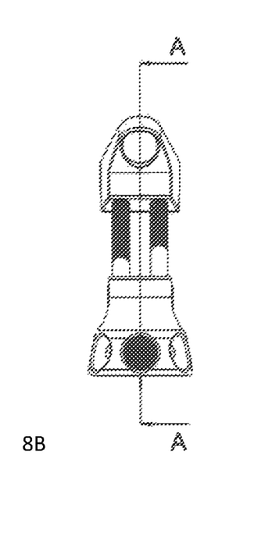
Figure 9:
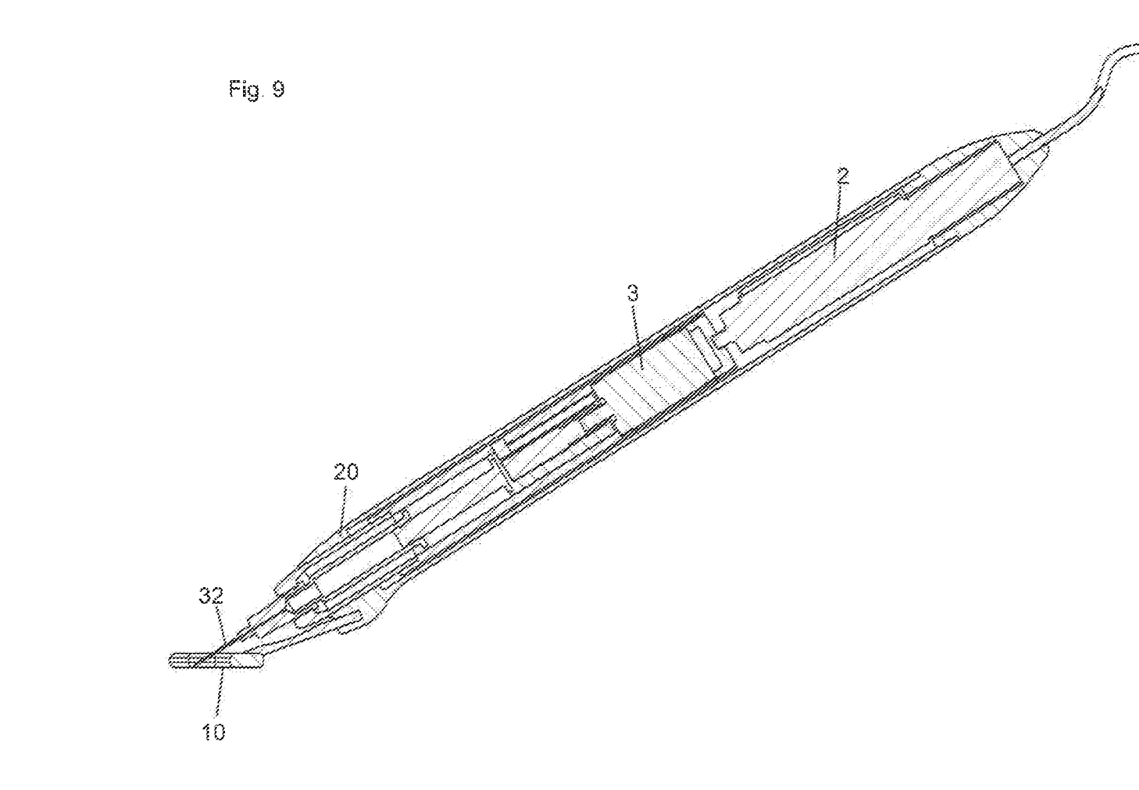
FIG. 9 shows a side view of a further preferred embodiment of the injection device which is powered by electricity, wherein the injection needle is in the starting position.
Figure 10:
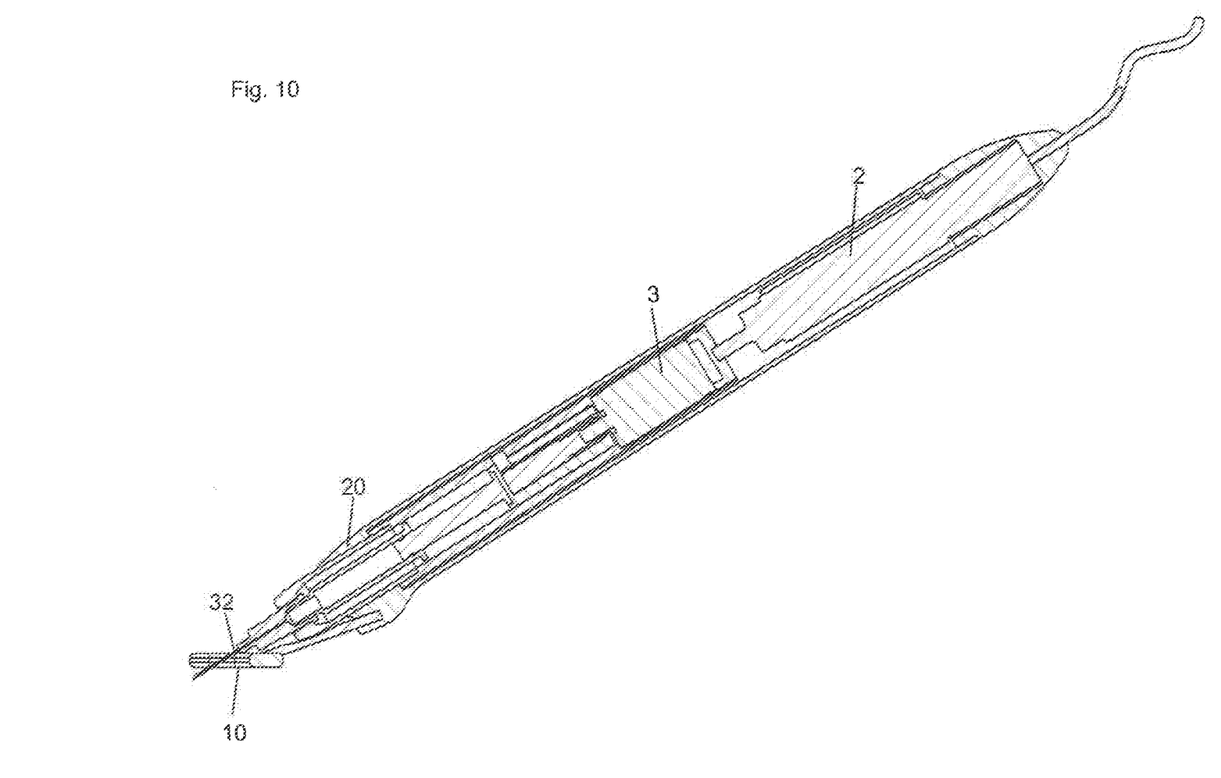
FIG. 10 shows a side view of a further preferred embodiment of the injection device which is powered by electricity, wherein the injection needle is in its fully injected position.

One distinct preferred embodiment of an injection device in accordance with the present invention is shown in side view in FIGS. 1, 2, 4 and 5 in longitudinal section in FIG. 3, and in perspective plan view in FIGS. 6 and 7. FIGS. 1, 3 to 5 and 7 show the injection device in retracted status. FIGS. 2 and 6 show the injection device in a state during injection. FIG. 8A shows a further longitudinal section and provides the sectional planes for the sections A-A and B-B which are shown in FIGS. 8B and C.

As can be seen from the FIGS. 1 to 8, the injection device comprises a head section as application element (10) in form of a head section for the application on the body of a subject, for example the scalp of a subject. The head section (10) comprises an upper part (11) and a lower part (12) which has an opening (13) and is directed to the body of the subject. The injection needle housing (20) is coupled to the head section (10) and comprises an upper channel (21) and a lower channel (22) and a further lower channel, which includes a stabilizing element, such as a pin, in particular a cylinder pin. The injection device comprises a first slide (30) with a holder for an injection needle (31) which comprises a hollow injection needle (32) with an opening, whereby the injection needle which comes out from the injection needle housing through the opening (13) from the head section (10). The first slide (30) is constructed such that it comprises a cut-out for a syringe, wherein this cut-out is leading into a protruding tube-formed element (33). Further, the slide (30) has a front channel, which can include a stabilizing element, like the pin, in particular the cylinder pin. The slide (30) comprises further a rear channel (34), and a continuous front to rear channel (35). The protruding tube-formed element (33) fits into the upper channel (21) of the injection needle housing (20). The injection device comprises a second slide (40) comprising means for holding the piston of a syringe (41), which is an element with protruding form. The second slide (40) comprises two continuous front to rear channels (42, 43), a rear channel, which comprises means for the retraction mechanism, and a release element (44). The first slide (30) is connected to the second slide (40) over a piston of a syringe (50). The injection device comprises further a first guide rail (60) having grooves on the surface which is fixed within the rear channel (34) of the first slide (30) and passes through one of the front to rear channels (43) of the second slide (40), and a second guide rail (70) having grooves on the surface which is fixed within the injection needle housing (20) and passes through the continuous front to rear channel (35) of the first slide (30) and through the front to rear channel (42) of the second slide (40); and wherein the second slide (40) comprises two leaf springs (46, 47) which engage with the grooves of the first guide rail (60) and the grooves of the second guide rail (70) and thus function as a ratchet mechanism. The ratchet mechanism is composed of the first leaf spring (46) which engages with the grooves of the first guide rail (60) and functions together with the first slide (30) as a drive mechanism for the injection movement. The second slide (40) further includes a ratchet mechanism composed of the second leaf spring (47) and the second guide rail (70), wherein the second leaf spring (47) engages with the grooves on the second guide rail (70). This ratchet mechanism together with the first slide (30) and a spring (80) included within the first slide (30) provide a retraction mechanism for the retraction movement of the injection needle (32) until it returns to its starting position. In the starting position the injection needle (32) covers the opening (13) of the head section only partially. Accordingly, in the case where the injection device has an opening within the upper part or additionally comprises a magnifying glass in this upper part, the top of the injection needle can be seen in the starting position. This allows the control of the application of the injection needle to a specific site. The release element (44) allows a free movement of the second slide (40). This movement is achieved with a distinct geometrical form of the release element (44). Accordingly it is foreseen that the release element (44) has a protruding element (48). The releasing of the second slide (40) is conducted with the movement of the release element (44) in the opposite direction of the injection movement. Thereby a pressure spring (49), which is held up on a cover (45), is compressed by the protruding element (48). This compression allows that the release element (44) is pushed again to its starting position. The cover (45) is screwed at the end of a clamp bolt (51). This clamp bolt (51) serves as guidance for the pressure spring (49) and the release element (44), in addition, the cover (45) is screwed at the end of this clamp bolt (51). During the release movement the protruding element (48) lifts the first and the second leaf spring (46, 47) from the grooves of the guide rails (60, 70), which allows a free movement of the second slide (40).

Example 2: Electrical Injection Device

Figure 11:
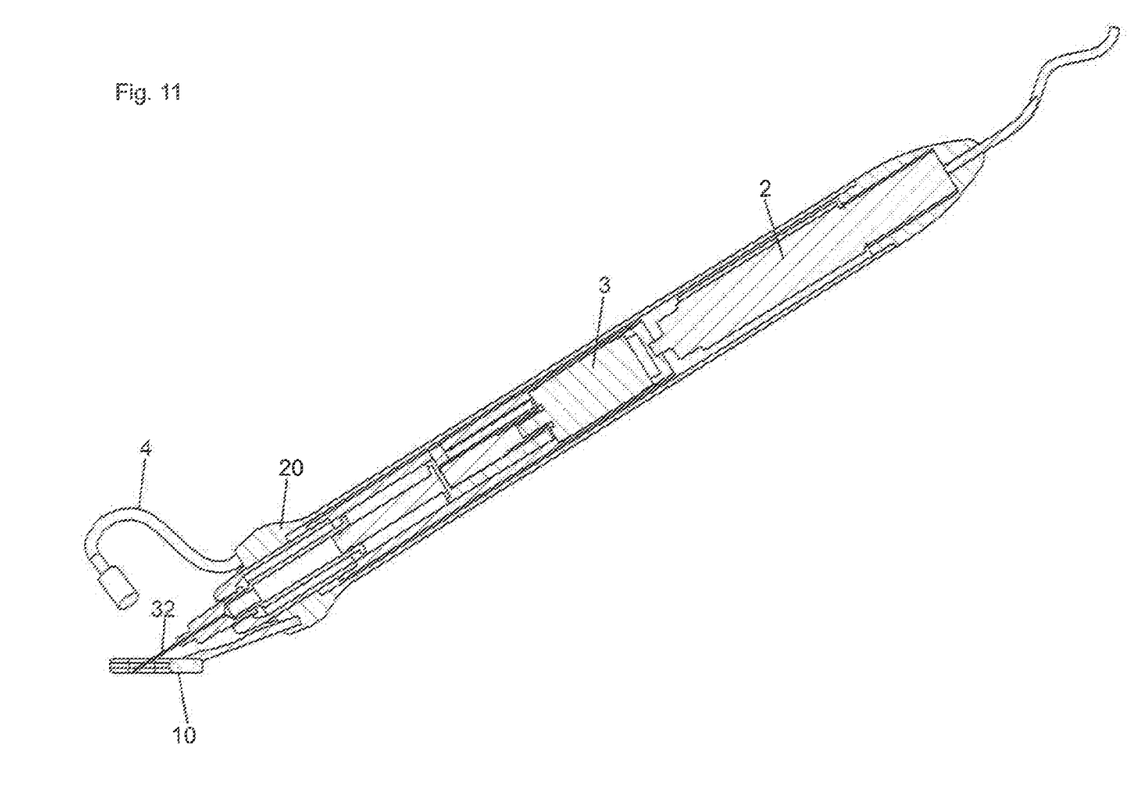
FIG. 11 shows a side view of a further preferred embodiment of the injection device which is powered by electricity including means for lighting.
Figure 12:
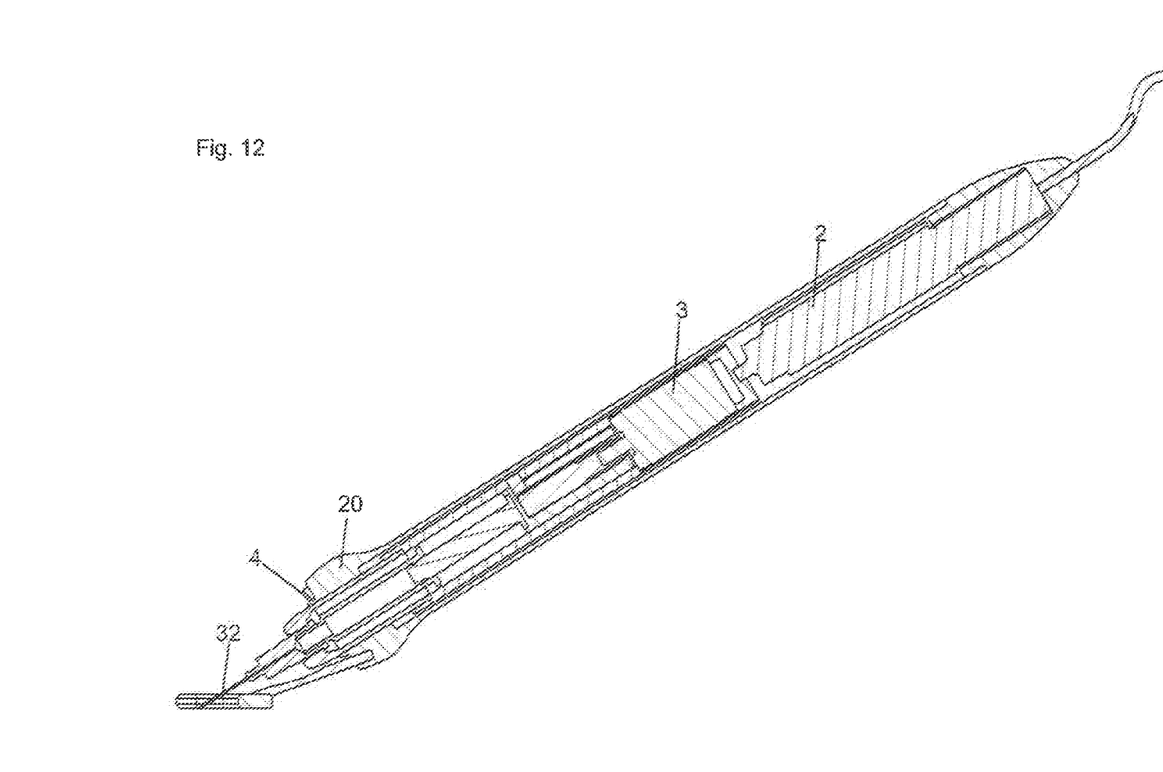
FIG. 12 shows a side view of a further preferred embodiment of the injection device which is powered by electricity including means for lighting, wherein the means for lighting are included in the injection needle housing.

A further distinct preferred embodiment of the present invention is shown in the FIGS. 9 to 12. As can be seen in these FIGS. 9 to 12, the injection device comprises a head section as the application element (10) which can be applied, for example, to the scalp of a subject. The injection needle housing (20) includes the injection needle (32) and further a syringe with a piston. During the injection movement, it is foreseen that the micro linear pusher (2) mediates the forward and reverse movement of the injection needle (32). The injection of the liquid is conducted with the motor (3) which allows that the piston of the syringe is pushed forward thereby injecting the liquid via the injection needle (32). The motor (3) leads to the rotation of the lead screw. The screw nut remains rotation-locked and transforms the rotation movement into a linear movement. The screw nut thereby exerts a push which results in the injection of the liquid through the forward movement of the piston of the syringe. The motor is adjusted to mediate the injection of the liquid only during the retraction movement. FIGS. 11 and 12 illustrates a further preferred embodiment of the injection device of the present invention which includes means for lighting (4).

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An injection device for introducing a substance into the body of a subject, the injection device comprising:
   an application element;
   at least one injection needle;

an injection needle housing;
a drive system for the injection movement, wherein the drive system comprises a micro linear pusher; and
a retraction system for a retraction movement, wherein the substance is injected during the retraction movement of the injection needle, and wherein the injection of the substance is conducted with an injection system comprising a motor, a lead screw and a screw nut.

2. The injection device of claim 1 wherein the micro linear pusher mediates forward and reverse movement of the at least one injection needle.

3. The injection device of claim 1 wherein the screw nut transforms a rotation movement of the motor and lead screw into a linear movement of the screw nut.

4. The injection device of claim 3 further comprising a syringe with a piston, wherein the screw nut exerts a push on the piston of the syringe during the linear movement of the screw nut.

5. The injection device of claim 4 wherein:
the syringe comprises a liquid; and
the push on the piston of the syringe results in injection of the liquid.

6. The injection device of claim 5 wherein the motor is adjusted to mediate the injection of the liquid only during a retraction movement of the device.

7. The injection device of claim 1 further comprising a means for lighting.

8. The injection device of claim 1 wherein the application element is configured for application to the scalp of a subject.

* * * * *